United States Patent [19]

Robinson

[11] Patent Number: 4,648,873
[45] Date of Patent: Mar. 10, 1987

[54] ADAPTER FOR INTRAVENOUS DELIVERY SET

[75] Inventor: Thomas P. Robinson, Plano, Tex.

[73] Assignee: Quest Medical, Inc., Carrollton, Tex.

[21] Appl. No.: 731,013

[22] Filed: May 6, 1985

[51] Int. Cl.⁴ ............................................. A61B 19/00
[52] U.S. Cl. ..................................... 604/411; 604/251
[58] Field of Search ................ 604/122, 251, 405, 411

[56] References Cited

U.S. PATENT DOCUMENTS

| | | | |
|---|---|---|---|
| 2,852,024 | 9/1958 | Ryan | 604/251 |
| 3,542,240 | 11/1970 | Solowey | 604/411 |
| 3,831,813 | 8/1974 | Latham, Jr. | 604/405 |
| 3,868,965 | 3/1975 | Noiles et al. | 604/411 |
| 4,505,709 | 3/1985 | Froning et al. | 604/411 |
| 4,507,113 | 3/1985 | Dunlap | 604/411 |
| 4,548,600 | 10/1985 | Ruschke | 604/122 |
| 4,576,594 | 3/1986 | Greenland | 604/251 |

FOREIGN PATENT DOCUMENTS 2105695  3/1983  United Kingdom ................ 604/411

Primary Examiner—C. Fred Rosenbaum
Assistant Examiner—Sherri E. Vinyard
Attorney, Agent, or Firm—Roger Clapp

[57] ABSTRACT

An adapter for enabling use with bags or bottles of an intravenous administration set having a proximal syringe venting connector with an air cannula. The adapter has a hollow body with threads for engaging the connector, and a spike for piercing an I.V. container, the spike having spaced fluid paths one of which is adapted to receive the connector air cannula.

4 Claims, 4 Drawing Figures

ADAPTER FOR INTRAVENOUS DELIVERY SET

TECHNICAL FIELD

This invention relates to intravenous administration sets, and more particularly to an adapter which may be used to convert an intravenous delivery set having a proximal connector for venting a disposable syringe into a set usable with an intravenous bottle or bag.

BACKGROUND ART

Intravenous administration sets have been known for many years incorporating at the proximal end of the tubing set, a spike for piercing the outlet of an intravenous fluid container such as a bag or a bottle. When an intravenous bottle is used, the spike typically has both a liquid flow path for conducting the liquid outwardly from the bottle as well as a separate air venting path for permitting air to enter the bottle to fill the space previously occupied by the outwardly flowing liquid. In the case of flexible intravenous bags, such an air vent path has not been necessary, since the bag will collapse as the fluid therein is depleted.

In addition to these traditional methods of connecting an I.V. container, there is also available in the trade administration sets having a connector suitable for securement to the outlet of a disposable syringe. This type of a syringe-venting connector, which enables the use of an inexpensive disposable syringe as a passive I.V. container, delivers the liquid without depression of the syringe plunger by permitting the venting of air into the body of the syringe. Such a connector is described in co-pending application Ser. No. 06/590,982, entitled "Parenteral Fluid Administration Apparatus and Method", which is owned by the assignee of this application.

This invention is directed to a unique adapter for increasincreasing the versatility of an I.V. administration set which incorporates this form of proximal syringe-venting connector.

SUMMARY OF THE INVENTION

The invention of this application contemplates an adapter used in combination with a syringe-venting connector which connector is formed with an inlet, an outlet, a liquid flow path therethrough conveying liquid in a first direction, a separate air vent conduit extending centrally of the liquid flow path outwardly of the connector inlet for venting air in the direction opposite said first direction, and having fastening means adjacent the connector inlet for engaging a threaded syringe outlet. The adapter includes a hollow body having threads for secure engagement to the inlet of the syringe-venting connector, a spike for piercing an I.V. liquid container, said spike extending from the hollow body and having a liquid path therein which communicates with the liquid path of the connector when the body is engaged with the connector. The hollow body of the adapter carries means for preventing the exit of air from the connector air vent conduit within the path of the liquid flowing through the adapter and connector flow path in said first direction. In a specific embodiment of the invention, the spike is formed with two separate spaced paths, the first of which forms part of the liquid flow path and a second of which receives the end of the connector air vent conduit extending from the connector inlet, whereby air entering the connector air vent is conducted upwardly through the second path of the spike to a venting site spaced from the principal path of liquid movement through the liquid flow path formed by the joined adapter and connector.

BRIEF DESCRIPTION OF THE DRAWINGS

A more complete understanding of the invention can be had by referring to the following detailed description together with the accompanying drawings wherein.

DETAILED DESCRIPTION

Figure 1:
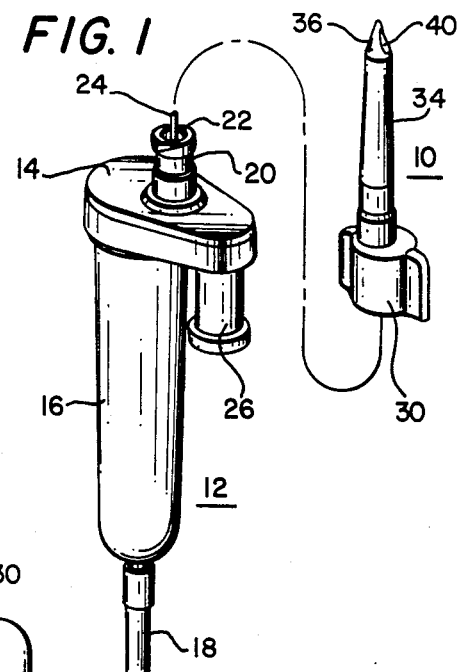
FIG. 1 is a perspective view showing the proximal end of an intravenous administration set having a syringe-venting connector and an adapter therefore formed in accordance with this invention.

Referring now to FIG. 1, there is depicted an adapter 10 constructed in accordance with this invention for securement to the proximal end of an intravenous administration set 12 having a syringe venting connector 14. Connector 14, when not used in combination with the adapter of this invention, is of the type known in the prior art for enabling connection of an I.V. administration set to a disposable syringe for permitting the syringe to be used as a passive I.V. container. Connector 14 has an outlet 16 in the form of a standard I.V. drip chamber connected to delivery tubing 18. Threaded inlet 20 extending from the connector 14 is adapted for securement to the outlet of a standard disposable syringe. Inlet 20 defines a flow path 22 when movement of liquid in a first direction downwardly through connector 14 and out outlet 16. Connector 14 also carries an air venting conduit 24 positioned centrally of the liquid flow path 22 and terminating at its upper end outside inlet 20. Air vent entrance 26 is formed on connector 14, permitting entrance of ambient air into the connector and upwardly through air vent conduit 24 in a direction opposite of the liquid flow down through flow path 22.

Connector 10 constructed in accordance with this invention enables the I.V. administration set 12 to be used for applications other than delivery from disposable syringes. Connector 10 is a hollow body 30 having internal threads 32 for secure engagement with the inlet of connector 14. A spike 34 for piercing the seal of an intravenous bag or bottle extends upwardly from the body 30. Spike 34 carries a first conduit 36 extending upwardly through the first side of spike 34 and communicating at its lower end 38 with the interior of hollow body 30. Spike 34 also forms a second flow path 40 extending the length of spike 34 on the side opposite liquid flow path 36.

Figure 2:
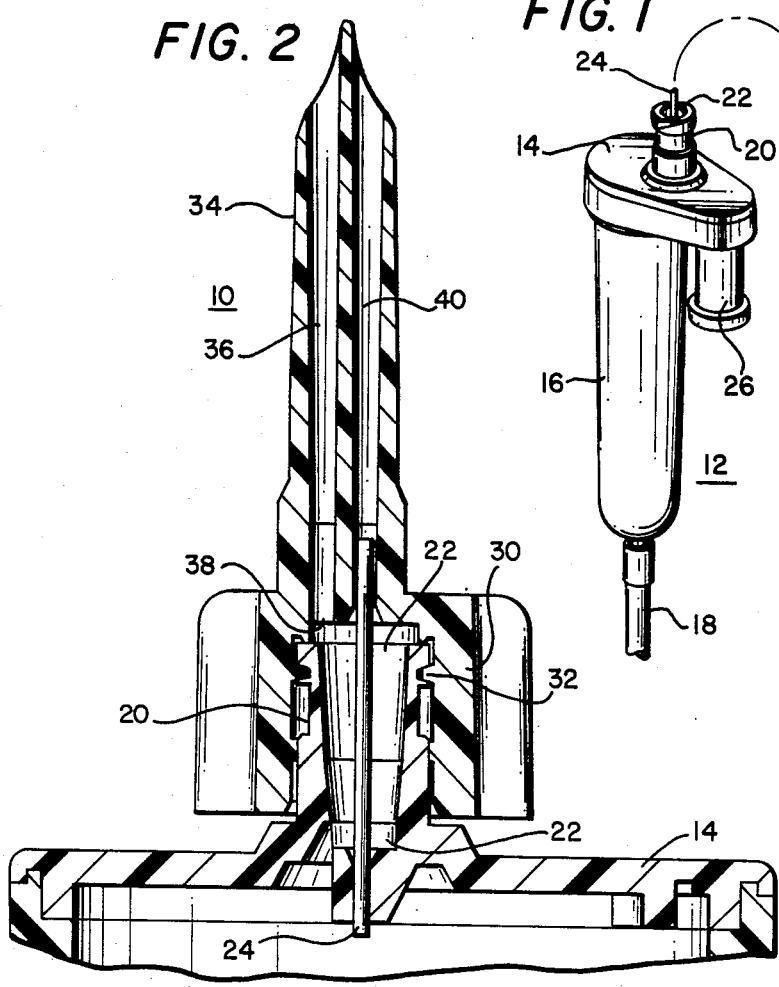
FIG. 2 is a cross sectional view of the adapter of this invention secured to a syringe venting connector.
Figure 3:
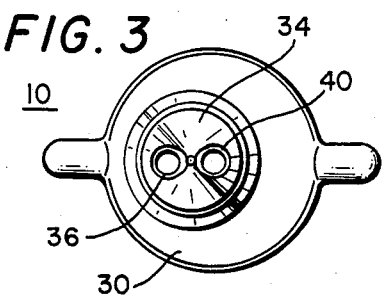
FIG. 3 is an end-view of the adapter illustrated in FIGS. 1 and 2, looking from the spike end.
Figure 4:
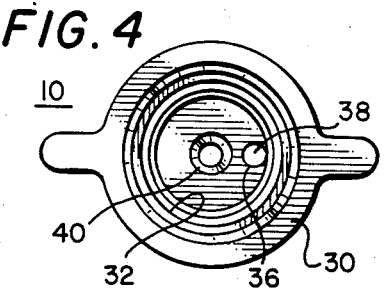
FIG. 4 is an end-view of the adapter taken from the end opposite the spike end.

The connector 10 is used in the event that the hospital wishes to employ an intravenous administration set having a syringe venting connector 14 in an application other than delivery of fluids from a syringe. When it is desired to deliver fluids using set 12 in conjunction with an ordinary I.V. bag or bottle, adapter 10 is secured to the inlet 20 of connector 14, converting the set to one which may be used with ordinary I.V. containers. As illustrated in FIG. 2, the securement of adapter 10 to connector 14 creates a continuous liquid flow path for flow of liquid downwardly through the proximal end of the set. This path comprises first flow path 36 through the spike, communicating with the interior of hollow body 30, and with the connector flow path 22, permitting liquid flow out through connector 16 and on to the patient through tubing 18. The second flow path 40 of spike 34 snugly engages the air vent conduit 24 extending from connector 14. Preferably, the wall of path 40 does not have an interference fit with air vent conduit 24. So engaged, the adapter 10 thus prevents the air which enters entrance 26 and bubbles upwardly through air vent conduits 24 from being swept back into delivery tubing 18 by the liquid flowing downwardly through the set. The air is vented at the upper end of path 40 spaced from the principal fluid flow path 36 by being on opposite sides of the spike.

It will be appreciated that the adpater of this invention represents a material advantage for users of I.V. administration sets. It is possible for a hospital to stock as a standard item the administration sets having the syringe venting connector which is advantageous to economical delivery of drugs through inexpensive disposable syringes. Hospital personnel can, by the very quick and simple attachment of adapter 10 to such a set, convert the set to normal usage with traditional intravenous containers.

Although a specific embodiment of the invention has been illustrated in the accompanying drawings and described in the foregoing detailed description, it will be understood that the invention is not limited to the embodiment disclosed, that it is capable of numerous rearrangements, modifications and substitutions of parts and elements without departing from the spirit of the invention.

I claim:

1. In combination with a syringe-venting connector having an inlet, an outlet, a liquid flow path therethrough for conveying fluid in a first direction, a separate air vent conduit extending centrally of the liquid flow path outwardly of the inlet for venting air in the direction opposite said first direction, the air vent conduit extending essentially concentric with the axis of symmetry of the inlet, and having fastening means adjacent the connector inlet for engaging a threaded syringe outlet, an IV container adapter for releasable securement to the connector comprising:
    a hollow body having means for secure engagement to the connector inlet;
    a spike for piercing an I.V. fluid container, said spike extending from the hollow body and having a liquid flow path therein which communicates with the liquid flow path of the connector when the body is engaged with the connector, the opening of the liquid flow path in the spike into the liquid flow path of the connector being radially spaced from the axis of symmetry; and
    means carried by the hollow body being essentially concentric with the axis of symmetry when the body is engaged to the connector to prevent the exit of air from the connector air vent conduit within the path of the liquid flowing through the adapter and connector flow path in said first direction.

2. The combination of claim 1 wherein said means for preventing the exit of air is comprised of a second path which receives the end of the air vent conduit extending from the connector inlet, the portion of the second path receiving the end of the air vent conduit being essentially concentric with the axis of symmetry whereby air entering the connector air vent conduit is conducted upwardly through the second path of the spike to a venting site spaced from the principal path of fluid movement through the liquid flow path.

3. An adapter for enabling an administration set having a syringe-venting connector to be used with intravenous bags and bottles, wherein the connector has an inlet and an air vent conduit extending centrally outward from the inlet along a central axis, comprising:
    a hollow body;
    means carried by the hollow body for engaging the connector inlet;
    a spike formed on the hollow body for piercing an I.V. container;
    a liquid flow path extending from a first location near the spike point into the interior of the hollow body; and
    an air vent flow path dimensioned to snugly receive the connector air vent conduit when the hollow body is secured to the connector inlet, the portion of the air vent flow path receiving the connector air vent conduit being essentially concentric with the central axis when the hollow body engages the connector inlet, said air vent flow path extending through the spike to a second location spaced from the first location.

4. An adapter for enabling an administration set having a syringe-venting connector to be used with intravenous bags and bottles, wherein the connector has an inlet configured for connection to a syringe, said inlet including an inlet passage and a threaded portion for threadedly receiving a syringe, each formed concentric about a first axis, and an air vent conduit concentric with the first axis and extending through the passage exterior of the inlet, comprising:
    a hollow body defining a chamber opening at one end to receive the inlet of the connector, the walls of the chamber being threaded to receive the threaded portion of the inlet to engage the adapter on the connector by rotating the adapter about the first axis relative to the connector to make up the threaded connection;
    a spike formed on the hollow body for piercing an I.V. container;
    a liquid flow path extending from a first location near the spike point into the chamber at a position spaced radially from the first axis; and
    an air flow vent path extending from a second location spaced from the first location near the spiked point and opening into the chamber, a portion of said air vent flow path extending from the chamber being concentric with the first axis to snugly receive the connector air vent conduit when the hollow body is secured to the connector inlet, said portion being oriented concentric with the first axis to maintain alignment between the portion and the connector air vent conduit as the threaded engagement between the connector and adapter is made up.

* * * * *